United States Patent
Cree et al.

[11] Patent Number: 5,947,945
[45] Date of Patent: Sep. 7, 1999

[54] DISPOSABLE ABSORBENT ARTICLE WITH FIT AND FLUID HANDLING CAPABILITIES

[75] Inventors: James W. Cree, Cincinnati, Ohio; Jennifer L. David, Amherst, Mass.

[73] Assignee: The Procter & Gamble Company

[21] Appl. No.: 08/743,061

[22] Filed: Nov. 4, 1996

Related U.S. Application Data

[63] Continuation of application No. 08/512,232, Aug. 7, 1995, abandoned.

[51] Int. Cl.$^6$ ..................................................... A61F 13/15
[52] U.S. Cl. ........................... 604/368; 604/378; 604/384; 604/385.1
[58] Field of Search .................................. 604/372, 377, 604/378, 379, 380, 384, 385.1

[56] References Cited

U.S. PATENT DOCUMENTS

| | | | |
|---|---|---|---|
| 2,331,355 | 10/1943 | Strongson | 128/290 |
| 2,662,527 | 12/1953 | Jacke | 128/290 |
| 3,897,782 | 8/1975 | Tunc | 128/290 |
| 4,011,871 | 3/1977 | Taft | 128/284 |
| 4,107,364 | 8/1978 | Sisson | 428/196 |
| 4,342,314 | 8/1982 | Radel et al. | 128/287 |
| 4,425,130 | 1/1984 | DesMarais | 604/389 |
| 4,576,596 | 3/1986 | Jackson et al. | 604/378 |
| 4,585,449 | 4/1986 | Karami | 604/378 |
| 4,592,751 | 6/1986 | Gegelys | 604/368 |
| 4,627,848 | 12/1986 | Lassen et al. | 604/370 |
| 4,781,710 | 11/1988 | Megison et al. | 604/378 |
| 4,787,896 | 11/1988 | Houghton et al. | 604/385 |
| 4,842,594 | 6/1989 | Ness | 604/368 |
| 4,880,417 | 11/1989 | Yabrov et al. | 604/355 |
| 4,973,325 | 11/1990 | Sherrod et al. | 604/368 |
| 5,007,906 | 4/1991 | Osborn, III et al. | 604/385 |
| 5,011,480 | 4/1991 | Gossens et al. | 604/385 |
| 5,037,418 | 8/1991 | Kons et al. | 604/387 |
| 5,092,860 | 3/1992 | Pigneul | 604/380 |
| 5,134,007 | 7/1992 | Reising et al. | 428/78 |
| 5,200,248 | 4/1993 | Thompson et al. | 428/131 |
| 5,217,445 | 6/1993 | Young et al. | 604/385 |
| 5,236,428 | 8/1993 | Zajaczkowski | 604/385 |
| 5,248,309 | 9/1993 | Serbiak et al. | 604/368 |
| 5,281,208 | 1/1994 | Thompson et al. | 604/378 |
| 5,295,988 | 3/1994 | Muckenfuhs et al. | 604/385 |
| 5,300,054 | 4/1994 | Feist et al. | 604/378 |
| 5,324,278 | 6/1994 | Visscher et al. | 604/385 |
| 5,334,289 | 8/1994 | Trokhan et al. | 162/358 |
| 5,382,245 | 1/1995 | Thompson et al. | 604/378 |

FOREIGN PATENT DOCUMENTS

| | | | |
|---|---|---|---|
| 8929891 | 5/1992 | Australia | 604/378 |
| 6782590 | 6/1992 | Australia | 604/378 |
| 2653328 | 4/1991 | France | 604/385.1 |
| 5-28327 | 4/1993 | Japan . | |
| 5-115506 | 5/1993 | Japan . | |
| 7-13318 | 3/1995 | Japan . | |
| 7-33315 | 6/1995 | Japan . | |
| 2168612 | 12/1984 | United Kingdom . | |
| 9103999 | 4/1991 | WIPO . | |

*Primary Examiner*—Mickey Yu
*Assistant Examiner*—Francis K. Cuddihy
*Attorney, Agent, or Firm*—Larry L. Huston; Jeffrey V. Bamber; J. Daniel Lykins

[57] ABSTRACT

An absorbent article comprises a liquid permeable topsheet, a liquid impermeable backsheet attached to the topsheet, an absorbent core of a combination of airlaid material, wetlaid material and superabsorbant, the core being positioned between the topsheet and the backsheet to absorb fluid, and wherein the core includes an elongated, cylindrical, raised portion for improved contact with a user, and a scrim material surrounding at least a portion of the raised portion of the core.

9 Claims, 4 Drawing Sheets

DISPOSABLE ABSORBENT ARTICLE WITH FIT AND FLUID HANDLING CAPABILITIES

This is a continuation of U.S. application Ser. No. 08/512,232 files Aug. 7, 195, now abandoned.

BACKGROUND OF THE INVENTION

The present invention relates to a thick disposable absorbent article which allows enhanced fit to the body and improved fluid handling. More particularly, this invention relates to a catamenial pad having a raised flexible strip consisting of absorbent oriented plastic netting system or "scrim" material in combination with acquisition, transfer and absorbent storage layers of core material; and wherein the core is able to become decoupled from the backsheet in the rear of the product. This invention is intended to also cover disposable diapers, panty liners, incontinent articles, sanitary napkins and the like.

Conventional catamenial pads or sanitary napkins comprise a liquid pervious topsheet, a liquid impervious backsheet joined with the topsheet, and a relatively flat absorbent core for storing fluid, positioned in between the topsheet and the backsheet. Conventional pads however, have several disadvantages in that when in use, they become deformed or detached, and do not provide a reliable fit or protection to the user. Usually, the entire pad's shape is integral, being restricted by the shape of the panty and will not move to conform to the users movements. In addition, as the pads are shifted and deformed as the user moves, the pads may leak.

Therefore, it is an object of the present invention to first, provide a product which has a scrim material which may be hydroentangled and is filled with fibers to provide a sustained fit to the body; secondly, provide a combination of airlaid and wetlaid tissues with a super-absorbent which serves as a unique fluid acquisition, distribution and storage system; and third, provide a core which is able to become decoupled from the backsheet either partially or in full, in the rear of the product to allow maximum lift during use of the product. The topsheet and backsheet attachment is designed in such a way that the core is unrestricted by the fit of the panty and can move with the body.

SUMMARY

In accordance with the present invention, an absorbent article is provided which comprises a liquid permeable topsheet; a liquid impermeable backsheet attached to said topsheet; an absorbent core of a combination of airlaid material, wetlaid material and superabsorbant, the core being positioned between the topsheet and the backsheet to absorb fluid, and wherein the core includes an elongated, cylindrical, raised portion for improved contact with a user; and a scrim material surrounding at least a portion of the raised portion of the core.

In accordance with a further aspect of the present invention, an absorbent article is provided which comprises a liquid permeable topsheet; a liquid impermeable backsheet attached to the topsheet; an absorbent core positioned between the topsheet and the backsheet, wherein the core consists of combination of airlaid and wetlaid tissues with superabsorbant and comprises an acquisition layer, an transfer layer and a storage layer, an elongated raised portion which acts as the acquisition layer of the core and contains fluid transporting fibers; a shaped strip of tissue which acts as the transfer layer and lies within the elongated strip and provides a channel for the fluid from the acquisition layer to the storage layer; means for decoupling the core from the backsheet in a rear portion of the article for lift, such that the core is unrestricted by the fit of an attached panty and can move with the user.

As used herein, the term "disposable absorbent article" refers to articles which absorb and contain body exudates and more specifically refers to articles which are placed against or in proximity to the body of a wearer to absorb and contain the various exudates which are discharged from the body (e.g., blood, menses, urine) and which articles are intended to be discarded after a single use (i.e. they are not intended to be laundered or otherwise restored or reused). A preferred absorbent article of the present invention would be used in a sanitary napkin or catamenial pad. As used herein the term "sanitary napkin" refers to an article which is worn by females adjacent to the pudendal region and which is intended to absorb and contain menstrual fluids and other vaginal discharges.

A super-absorbent is defined herein to mean materials which are capable of absorbing body fluid in quantities corresponding anywhere from several times to 60 times their own weight.

Throughout the specification, the "Z-direction" will be defined as the direction which is orthogonal to the plane of the sanitary napkin when it is in the flat, laid out position. The axis of the Z-direction is generally oriented towards the wearer while the sanitary napkin is worn. The X-Y plane is orthogonal to the Z-direction axis, encompasses the longitudinal and transverse axes and is coincident with the plane of the inwardly oriented surface of the backsheet when the sanitary napkin is in the flat, laid out position.

"Scrim" is defined herein to mean an oriented, plastic netting which can be made with varying flexibility.

"Pore size" as used herein is the wet pore size as measured in accordance with U.S. Patent entitled "Article with Fused Layers" to Cree.

BRIEF DESCRIPTION OF THE DRAWINGS

The invention will now be described by way of example and with reference to the accompanying drawings, in which.

DETAILED DESCRIPTION OF THE PREFERRED EMBODIMENT

Figure 1:
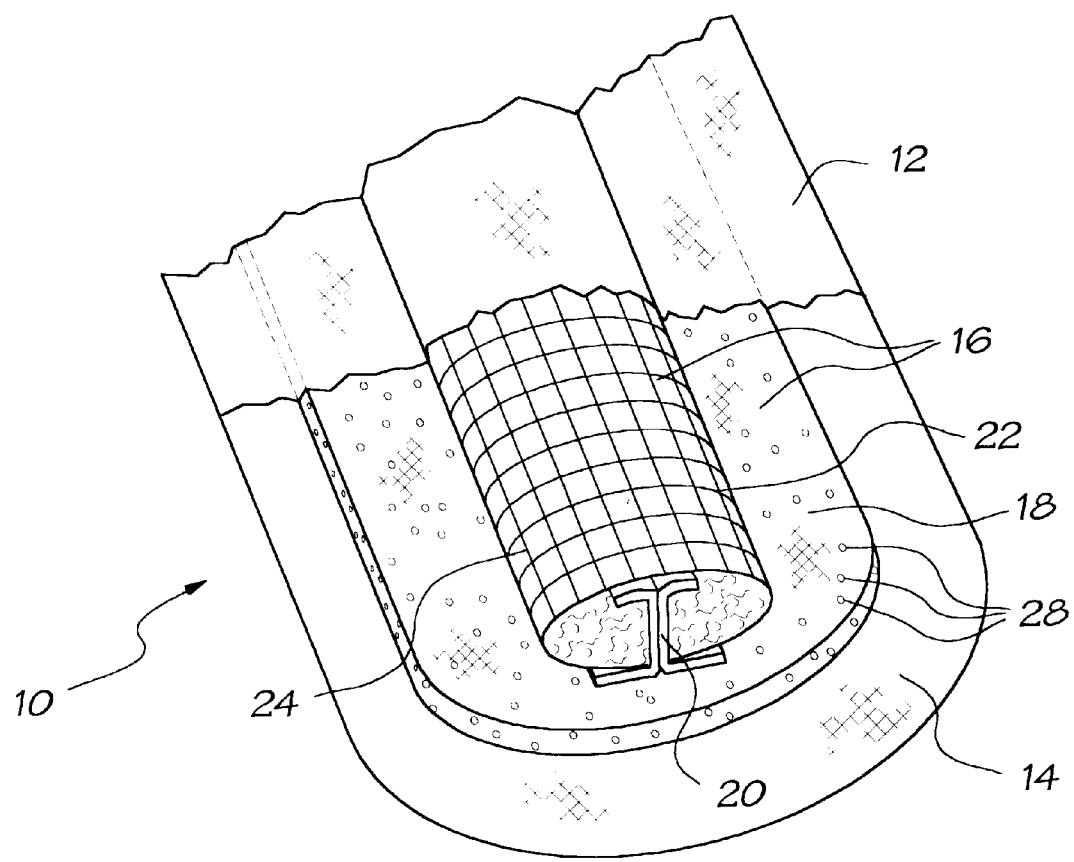
FIG. 1 is a pad according to the present invention.

It is an object of the present invention to provide a disposable absorbent article or catamenial pad with superior fit and fluid handling capabilities. In the application of the present invention, a disposable absorbent article 10 is provided which has a fluid permeable topsheet 12, preferably of continuous plastic material; a fluid impermeable backsheet 14, preferably of polyethylene film; and an absorbent core 16. The topsheet and the backsheet preferably are joined together either directly or indirectly through intermediate materials.

The topsheet is compliant, soft feeling and non-irritating to the wearer's skin. Furthermore, the topsheet is liquid pervious, permitting liquids to readily transfer through its thickness. A suitable topsheet may be made of a wide range of materials such as formed thermoplastic films, apertured plastic films, porous foam, reticulated foams, natural fibers (e.g. wood or cotton fibers), synthetic fibers (e.g., polyester or polypropylene fibers) or from a combination of natural and synthetic fibers with formed films being preferred. Preferably, the topsheet is made of continuous plastic material such as the apertured formed film as shown in U.S. Pat. Nos. 4,342,314 and 4,463,045. In addition, the topsheet is hydrophilic so that it helps transfer the liquid through the top sheet faster.

The backsheet is impervious to liquids and is preferably manufactured from a thin plastic film, although other select liquid impervious materials may also be used. The backsheet prevents the exudates which have been absorbed and contained in the absorbent core from wetting the article attached to the absorbent article, such as a panty in the case of a catamenial pad. Examples of materials used for the backsheet are polymeric materials such as polyethylene or polypropylene. The backsheet may also comprise a woven or non-woven material or composite materials such as film-coated non-woven material. An exemplary backsheet is a 1 mil thick polyethylene film.

The topsheet and the backsheet are joined together in any suitable manner. The topsheet may be directly secured to the backsheet with adhesive or other suitable means, or the topsheet may be indirectly secured to the backsheet by affixing the topsheet to intermediate members which in turn are affixed to the backsheet.

The absorbent core is positioned in between the topsheet and the backsheet. The absorbent core provides a further benefit to the invention and serves as a unique fluid acquisition and distribution system. The absorbent core should be generally compressible, conformable and non-irritating to the wearer's skin, and capable of absorbing and containing liquids and certain body exudates. The preferred core material in accordance with the present invention is a layered combination of airlaid and wetlaid materials and superabsorbant and contains an absorbent gelling material known as AGM 28 which is a starch-based product which swells when wet. The core 16 is comprised of three parts each having distinct properties. The first part, closest to the body is the acquisition layer 22. It contacts the fluid. Then the second layer, the transfer or distribution layer 20 transports the fluid to the third layer, the storage layer 18.

The pad of the present invention is preferably a coretube. A core tube is a tube-like element which is placed on a thin pad as described in U.S. Pat. No. 4,425,130 to DesMarais.

An oriented net polymeric material or scrim tube is provided over the tube-like element in accordance with the present invention, as shown in FIG. 1. This provides for sustained fit to the body, resiliency and enhanced fluid handling. The scrim system 24 is preferably porous polypropylene plastic and is formed in the shape of an elongated cylindrical tube which is designed for optimum body contact. This scrim tube is over and attached to the ultra-absorbent storage layer 18 of the core. The scrim maintains the shape of the tube and avoids collapse when wet or compressed. Polyester fiber filler (not shown in FIG. 1) provides cushion within the scrim tube since the scrim is relatively stiff, thereby allowing resiliency to the product in the Z-direction. This scrim tube also maintains its shape when wet due to its hydrophobic nature. Therefore, wearer always feels dry. Therefore, even when the pad is saturated, the scrim will continue to allow additional fluid acquisition and fit because it maintains an open pore structure within the product due to its porosity.

The scrim allows for sustained body contact along three important regions of the body: introitus, perineum and the gluteal groove. The use of a raised, highly flexible and scrim-covered tube provides sustained body contact at the three critical areas of the body, independent of position of the panty and the movement of the user. Once the fluid has been acquired by the insert, the fluid is transferred to the core of the product, where it can be absorbed and stored away from the body, keeping the user dry.

The scrim may be hydroentangled with fibers. This is achieved by entangling hydrophilic and absorbent fibers onto the scrim using a battery of water jet nozzles which force the fibers into the scrim netting. When hydroentangled, the scrim can provide superior fluid handling benefits since these fibers, depending on their selection, allow directional fluid movement along the scrim and provide capillaries for temporary fluid storage area until the fluid is moved into the storage portion of the core. Once drained, the fibers help the user feel dry and more comfortable as the "stay dry" fibers mask the fluid.

The scrim material itself can be made from a variety of olefinic polymers and may be made by a variety of net making processes as are known in the art. The scrim can be made hydrophobic or hydrophilic by incorporating the right surfactant in the polypropylene or polyolefinic nature resin of the scrim. The diameter of the scrim tube could be altered in the front or the back to provide enhanced fit, allowing the tube to better conform to the contours of the body. In addition, the scrim is made more or less flexible, to allow for best fit to the body while retaining Z-direction resiliency. The technology of stretch scrim may be incorporated in the pad to provide for further flexibility and lift of the pad.

The fibers used to hydroentangle the scrim may be selected to provide fluid handling benefits and may be changed to create the desired direction of fluid movement on the scrim into the core. By altering the type and/or amount of fibers used, the material can be designed to move fluid in a straight "downward" distribution of the fluid or in a "wicking" action in the longitudinal direction of the pad based on the structure of the transfer layer. These fibers allow the fluid to pass straight through to the storage part of the core. Different types of fibers could be used, including those having round cross-sections and large denier fibers for a cushiony fit and more flexibility. Also, "Y" cross-sectioned hydrophilic fibers may be used and capillary channel fibers (CCF) which have intra-fiber capillaries in their longitudinal direction on either their interior or exterior surface, such as disclosed in U.S. Pat. Nos. 5,200,248 and 5,281,208 both to Thompson et al. These capillary channel fibers draw fluid away from the topsheet to provide a clean, dry appearance. Any of the above fibers could be used inside of the scrim tube, and may be hydrophobic or hydrophilic. The material for the fibers must be selected so that the fibers provide resiliency, a cushiony fit even when the pad is saturated, and rapid fluid transport down into the storage part of the core.

Figure 2A:
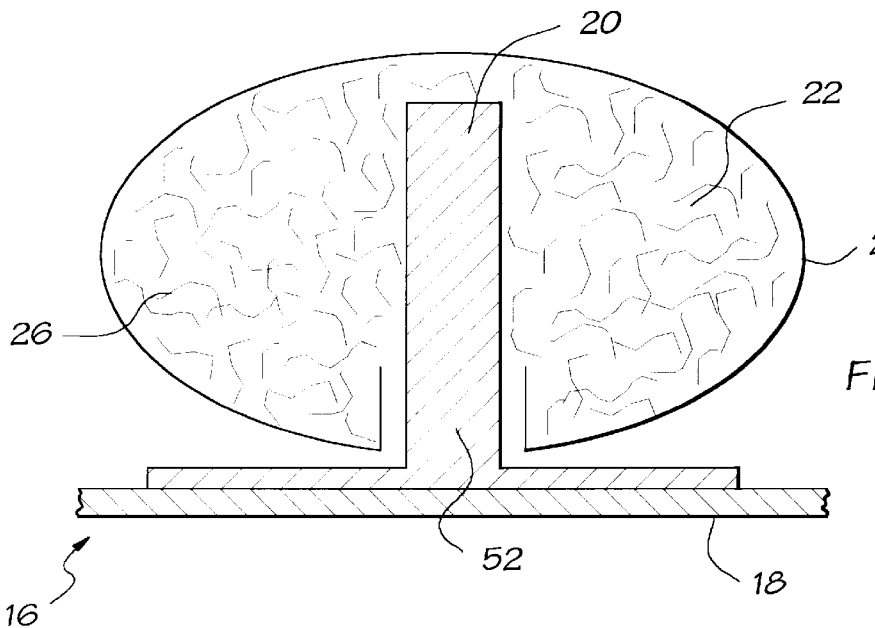
FIG. 2(a)–2(c) are various embodiments in accordance with the present invention.
Figure 2B:
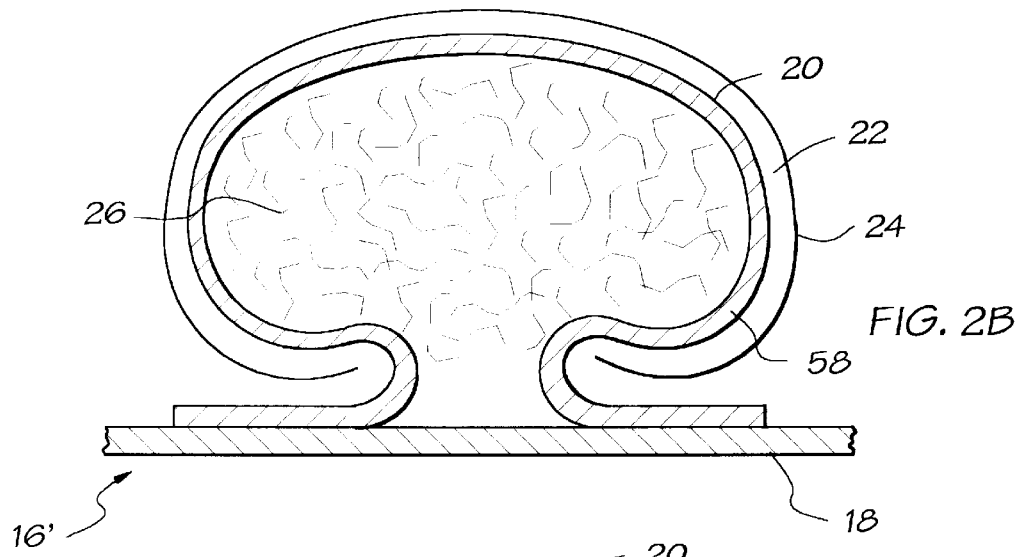
Figure 2C:
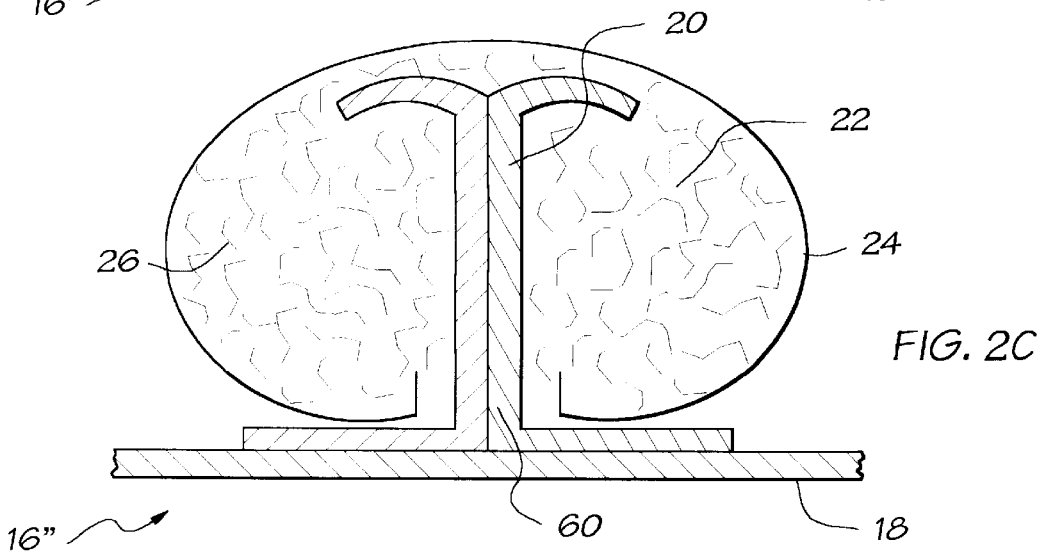

A uniquely shaped strip (transfer layer 20) is present inside the scrim tube 24 which helps move the fluid to the core (the main storage area 18). This provides for some of the pad's capacity, and serves to absorb any fluid trapped in the fibers which fill the absorbent scrim tube. In a preferred embodiment, this is a piece of absorbent wet laid tissue material with a pore size network much smaller than the surrounding tissue. The surrounding tissue typically has a pore size network of about 100 microns, whereas the wet laid material has a pore size network of about 25–35 microns. The wet laid material has smaller capillaries than the air laid material so that the fluid tends to move from larger capillaries to the smaller ones which provides the mechanism of fluid transport to the storage area. In addition, such a strip will have a hydrophilic contact angle which is much smaller than the surrounding fiber (i.e. 35° as compared to 89–91°). The strip is placed within the hydroentangled scrim tube to provide a channel for the fluid. This laminated material transports the fluid from the scrim, the introduction site, to the storage core of the pad where it can be stored. The shaped strip is preferably a wet laid material known as CPN. "CPN" as used herein is made as disclosed in U.S. Pat. No. 5,334,289 to Trokhan et al. The CPN inside of the scrim could be arranged in such a way so as to collect the fluid from the scrim and surrounding fibers and transmit it to the storage part of the core. An additional layer of CPN added between the core and the backsheet will prevent bunching of the absorbent article. FIG. 2(a)–2(c) show several cross-sections of FIG. 1 in accordance with several embodiments of the present invention showing only the core 16. In particular, several alternative transfer layer 20 portions of the core are shown. These CPN shapes include, but are not limited to, a laminate spike as shown in FIG. 2(a). In this embodiment, the transfer layer 20 consists of a spike of laminate 52, protruding into the fiber-filled 26 scrim 24. In FIG. 2(b) the transfer layer is continuous. A layer of formed-film transfer layer 20 is attached to the scrim 24 which is filled with fibers 26. An "I"-shaped laminate of transfer layer is shown in FIG. 2(c) in which the CPN laminate 60 is shaped like the letter I and protrudes into the fiber-filled 26 scrim 24 part of the core 50". This is the most preferred shape for transfer layer 20 since it utilizes advantages of both of the two aforementioned designs.

The CPN tissue material used in the tube may be substituted by a variety of small pore size flexible absorbent and wicking materials having an average pore size of 40–50 microns under 25 psi of pressure such as meltblown, wetlaid, cross-linked cellulose fibers such as those described in U.S. Pat. No. 5,217,445 to Young et al., or others. Any of these materials may or may not be laminated with superabsorbant material. The fibers that surround the absorbent gelling core laminate in the tube are used to provide a cushiony fit, making the product even more flexible and adaptable to the contours of the body.

Figure 3:
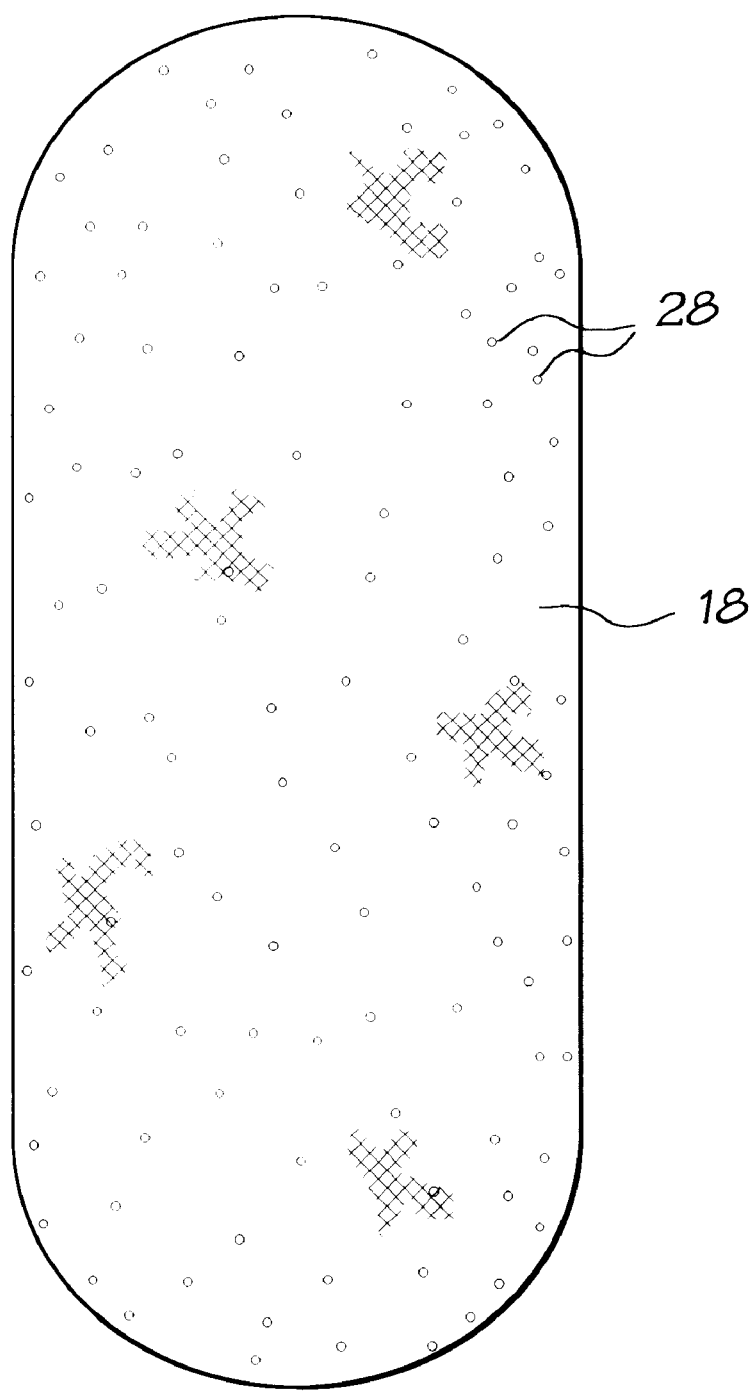
FIG. 3 shows a pad having Z-folding according to the present invention.

The storage part of the core 18 is an air laid laminate of AGM encapsulates on an air laid tissue. As an alternative, you can put a small amount of superabsorbant in the transfer layer in the CPN portion. However, this amount must be less than 10% of the total amount in the storage layer, so that the swelling of the superabsorbant does not interfere with the transfer of the fluid. The storage layer is airlaid or preferably wet laid material having a basis weight between 25–35 pounds/ream. It is folded upon itself and includes AGM encapsulates inside. The total capacity of such a layer is between 5–15 grams per gram, optionally, as shown in FIG. 3, the AGM is not incorporated into the entire area of the storage core 18. Since the majority of fluid flow reaches the center of the layer 18, it is desirable for the fluid to be held more evenly distributed within the storage layer. By having the AGM 28 only on the periphery of the layer, more fluid will flow to the outer regions for enhanced capacity of the storage layer.

It is known that a thinner pad provides greater comfort. Because of the high fluid capacity of this product, material could be removed from the core without sacrificing protection. Either the absorbent gelling material content could be lowered, or the number of core layers could be reduced. Exemplary materials for use in the core include thin absorbent materials, such as 1) an 18 grams per square yard (21.5 g/m$^2$) spun bonded polypropylene non-woven material known as CELESTRA available from Fiberweb, North America of Simpsonville, S.C., which is then embossed with the pattern described in U.S. Pat. No. 4,781,710 issued to Megison et al.; 2) a non-woven material with a thermally bonded polypropylene fibers such as the carded thermally bonded polypropylene non-woven web having a basis weight of 23 grams per square yard, available from Veratec, which is then embossed with the pattern described in U.S. Pat. No. 4,781,710 to Megison et al.; 3) meltblown polyethylene, 4) polypropylene, or 5) a wet laid tissue made as disclosed in U.S. Pat. No. 5,334,289 to Trokhan et al.(CPN) could be attached to the polymer backsheet.

The laminate core could also be altered to improve flexibility, by reducing the layers used, by alternating the core material, or by ring rolling. Ring rolling involves a corrugating process described in U.S. Pat. No. 4,107,364 to Sabee using toothed-rollers with intermeshing teeth.

The pad of the present invention allows for the three advantages as stated above; namely improved fit, improved fluid acquisition and distribution, and maximum movement of the core material during user movement. As for this last advantage, the pad is attached in such a way as to allow maximum lift of the core from the backsheet in the back of the product. This can be accomplished through a unique attachment of the core, topsheet and backsheet and is important since the scrim tube is relatively stiff. Specifically, the topsheet is attached, either directly or indirectly, to the backsheet. A special attachment of the core to the backsheet is provided which allows the core to decouple from the backsheet and achieve the desired lift and fit. This special attachment includes the use of either pleats in excess topsheet or backsheet material which enables the core to be removed from the backsheet while still being contained within the confines of the pad. The pad is decoupled from the backsheet either partially or in full, in the rear of the product to allow maximum lift during use of the product.

Figure 4:
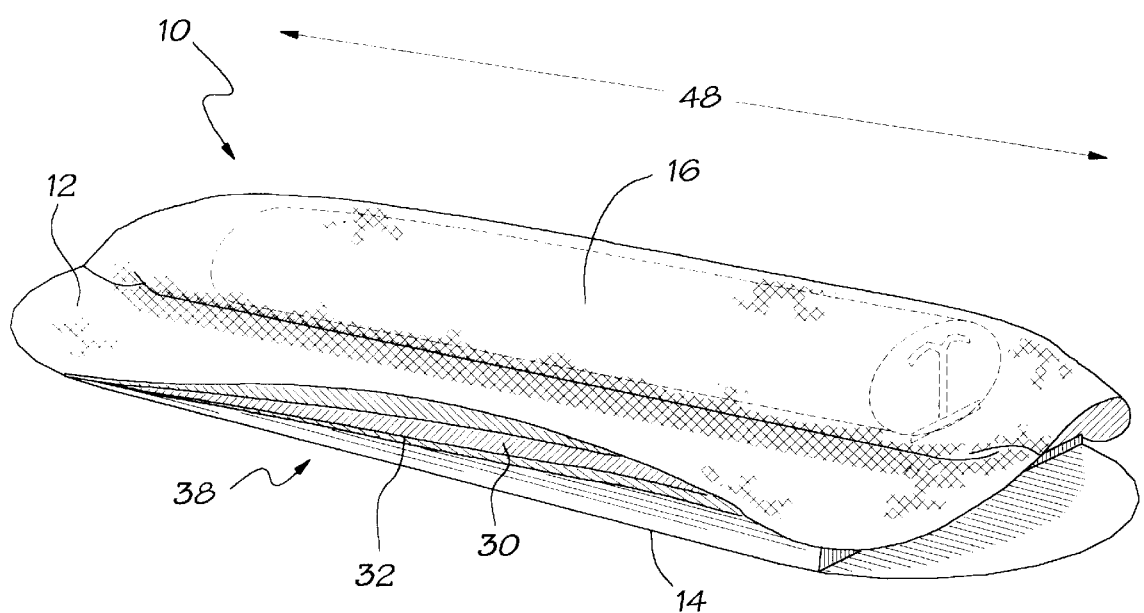
FIG. 4 is a prespective view of the present invention.

One suitable means for controlling decoupling, in accordance with one aspect of this invention is shown in FIG. 4. The backsheet 14 is decoupled in the Z-direction. The axis 48 of the Z-direction is generally oriented towards the wearer while the pad 10 is worn. The excess material 30 is folded in the shape of a Z or M by Z-folding, thereby allowing more backsheet material than topsheet 12 material. As the core 16 is lifted away from the panty-facing adhesive 38 and the subsequently attached backsheet 14, usually in the rear of the product, by movement of the wearer, the backsheet material remains stationary and the Z-folds 30 are extended from fold lines 32 to allow movement of the core. The longitudinally oriented pleats may be an extension of the topsheet 12, an extension of the backsheet 14, or a separate piece of material having one end joined to the topsheet 12 and one end joined to the backsheet 14. Preferably, two longitudinally oriented pleats are provided, one at each longitudinal end of the pad 10. With this allowed movement of the core, the protection is not interrupted and the backsheet does not become displaced from the panty or other material to which the absorbent article is attached. The core may be decoupled from the backsheet by any other suitable means that allows the core to decouple from the backsheet.

The scrim tube is attached to the core and the core is decoupled, preferably completely decoupled, from the backsheet as discussed above. Alternatively, some of the core material may remain attached to the backsheet while the remainder of the core is lifted. These features allow the product greater lift, flexibility and natural fit into the grooves of the body. The panty fastening adhesive could be altered to produce the best attachment to the panty while still allowing for the necessary lift of the core. When the pad decouples in use, the core could catch and retain any fluid which might be missed due to reduced area coverage of the core itself.

In summary, the core enhances and maintains the fit of the product and minimizes the contact area in order to reduce bunching. The shape of the product and the lift provided compensate for the reduced protection area.

Having described the invention in detail and by reference to preferred embodiments thereof, it will be apparent that modifications and variations are possible without departing from the scope of the invention defined in the appended claims.

What is claimed is:

1. An absorbent article comprising:

a liquid-permeable topsheet;

a liquid-impermeable backsheet attached to said topsheet;

an absorbent core positioned between said topsheet and said backsheet, wherein said core consists of a combination of air laid material, wet laid material and super absorbent, said core comprising an acquisition layer, a transfer layer and a storage layer, wherein said core is decoupled from said backsheet in a rear portion of said article for lift of said core with respect to said backsheet;

an elongated raised portion which acts as said acquisition layer of said core and contains fluid-transporting fibers;

a shaped strip of absorbent material lying within said elongated raised portion which acts as said transfer layer and provides a channel for said fluid from said raised portion to said storage layer such that said shaped strip has a cross-section selected from the group consisting of a laminate spike, an "I" shape, and a continuous strip connected within said raised portion; and a plastic netting material surrounding at least a portion of said raised portion of said core, said netting material being cylindrical in shape and closely conforming to said elongated cylindrical, raised portion of said core, wherein said plastic netting material provides sustained resiliency of fit and enhanced fluid handling of said elongated, cylindrical, raised portion of said core.

2. The absorbent article of claim 1 wherein said shaped strip has a laminate spike cross section and lies within said elongated raised portion.

3. The absorbent article of claim 2 wherein said shaped strip has an "I" shaped cross section and lies within said elongated raised portion.

4. The absorbent article of claim 2 wherein said shaped strip is continuous and is connected with and lies within said elongated raised portion.

5. The absorbent article of claim 1 wherein said backsheet is Z-folded to allow said core to decouple from said backsheet.

6. The absorbent article of claim 1 wherein said core is decoupled from said backsheet by Z-folding said backsheet.

7. The absorbent article of claim 1 wherein said core is decoupled from said backsheet by Z-folding said topsheet.

8. The absorbent article of claim 7 wherein said fluid transporting fibers are hydrophilic capillary channel fibers.

9. The absorbent article of claim 1 wherein said core further includes absorbent gelling material laminated within said core.

* * * * *